US00PP37022P2

(12) United States Plant Patent
Giesen

(10) Patent No.: US PP37,022 P2
(45) Date of Patent: Oct. 14, 2025

(54) ***PETUNIA* PLANT NAMED 'PEHY0092'**

(50) Latin Name: *Petunia hybrida*
Varietal Denomination: PEHY0092

(71) Applicant: SYNGENTA CROP PROTECTION AG, Basel (CH)

(72) Inventor: Eric Giesen, Andijk (NL)

(73) Assignee: Syngenta Crop Protection AG, Basel (CH)

( * ) Notice: Subject to any disclaimer, the term of this patent is extended or adjusted under 35 U.S.C. 154(b) by 0 days.

(21) Appl. No.: 19/217,337

(22) Filed: May 23, 2025

(51) Int. Cl.
*A01H 5/02* (2018.01)
*A01H 6/82* (2018.01)

(52) U.S. Cl.
USPC ..... Plt./356.1
CPC ..... *A01H 6/824* (2018.05)

(58) Field of Classification Search
USPC ..... Plt./356.1
CPC ..... A01H 5/02
See application file for complete search history.

*Primary Examiner* — Kent L Bell
(74) *Attorney, Agent, or Firm* — Dale Skalla

(57) ABSTRACT

A new *Petunia* plant named 'PEHY0092' particularly distinguished by its medium to large sized flowers. yellow flower color, early flowering and mounding plant habit.

1 Drawing Sheet

Latin name of the genus and species of the plant claimed: *Petunia hybrida.*

Varietal denomination: 'PEHY0092'.

BACKGROUND OF THE NEW PLANT

The present invention comprises a new *Petunia*, botanically known as *Petunia hybrida*, and hereinafter referred to by the variety name 'PEHY0092'.

'PEHY0092' is a product of a planned breeding program. The new cultivar has medium to large sized flowers, a yellow flower color, medium to late flowering and a mounding plant habit 'PEHY0092' originated from a hybridization made in October 2021 in a controlled breeding environment in Enkhuizen, The Netherlands. The female parent was the breeding line 'PETBE1201-1', 'Yellow Multiflora' (not patented). Compared to 'PEHY0092', it has a smaller plant size, is earlier flowering and has a darker yellow flower color.

The male parent of 'PEHY0092' was the breeding line 'PET20-1337-2' (not patented). 'PET20-1337-2' is a plant with a deep yellow flower color, bit cup shaped flowers, medium sized flowers, late flowering, and mounding to upright plant habit.

The resulting seeds were sown in January 2022. 'PEHY0092' was selected as one flowering plant within the progeny of the stated cross in May 2022 in a controlled environment in Enkhuizen, The Netherlands.

The first act of asexual reproduction of 'PEHY0092' was accomplished when vegetative stem cuttings were propagated from the initial selection in June 2022 in a controlled environment in Enkhuizen, The Netherlands.

BRIEF SUMMARY OF INVENTION

Horticultural examination of plants grown from cuttings of the plant initiated in June 2022 and continuing thereafter, has demonstrated that the combination of characteristics as herein disclosed for 'PEHY0092' are firmly fixed and are retained through successive generations of asexual reproduction.

'PEHY0092' has not been observed under all possible environmental conditions. The phenotype may vary significantly with variations in environment such as temperature, light intensity, and day length.

Plant Breeder's Rights for this cultivar have not yet been applied for. 'PEHY0092' has not been made publicly available more than one year prior to the filing of this application.

The following traits have been repeatedly observed and are determined to be basic characteristics of the new variety. The combination of these characteristics distinguishes this *Petunia* as a new and distinct variety.

BRIEF DESCRIPTION OF THE PHOTOGRAPHS

The accompanying photographic drawings show typical flower and foliage characteristics of 'PEHY0092' with colors being as true as possible with an illustration of this type.

Figure 1:
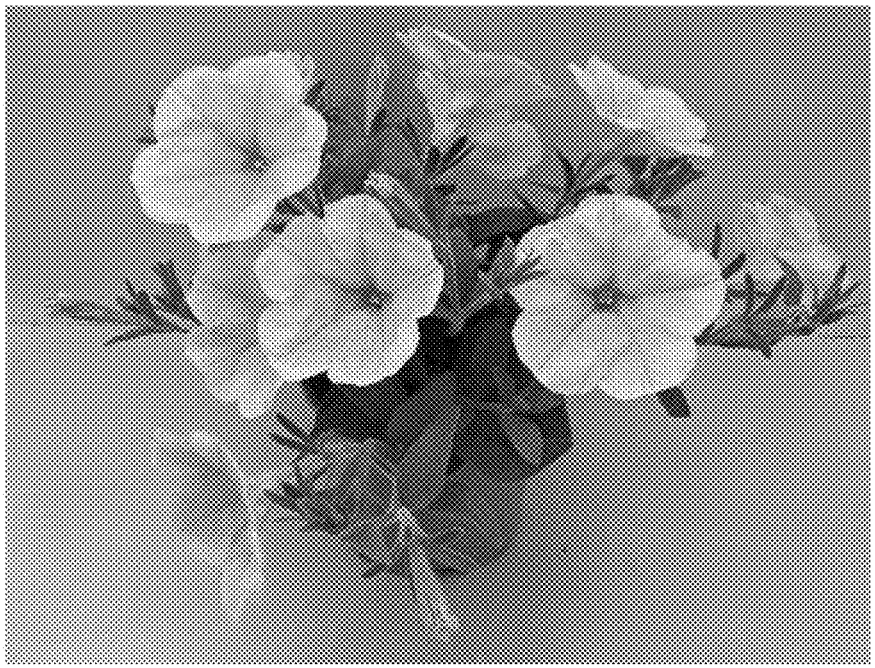
Figure 2:
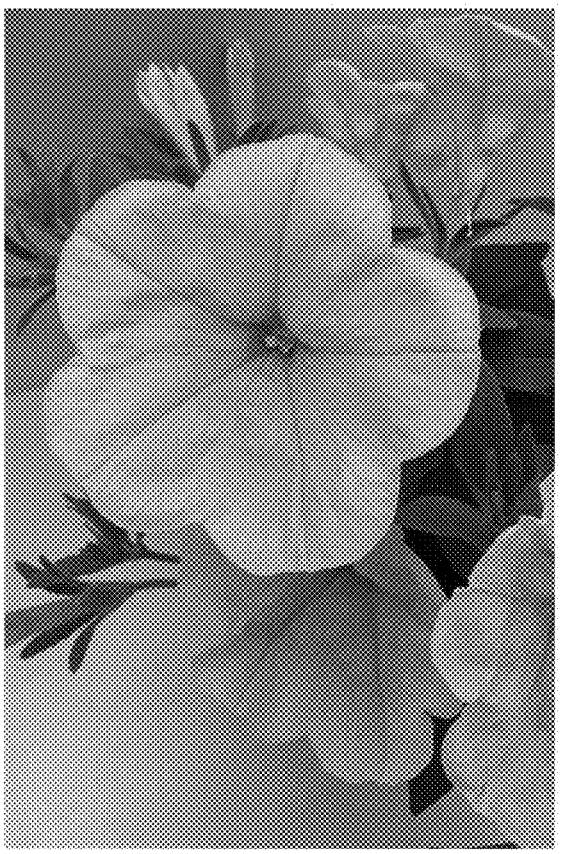

The photographic drawings show in FIG. 1 a flowering plant of the new variety and in FIG. 2 a close-up of the flowers.

DETAILED BOTANICAL DESCRIPTION

The aforementioned photographs were taken in May 2024 from plants growing indoor in 12 cm pots in Andijk, The Netherlands. These plants were approximately 12 weeks of age.

The plant descriptions and measurements were taken in June 2024 in Andijk, The Netherlands on outdoor plants grown in 35 cm containers. These plants were about 12 weeks old.

Color references are made to The Royal Horticultural Society Colour Chart (R.H.S.) 2001.

TABLE 1

DIFFERENCES BETWEEN THE NEW VARIETY 'PEHY0092' AND A SIMILAR VARIETY

| | 'PEHY0092' | 'Aurora Banana Candy', Not patented |
|---|---|---|
| Earliness: | Earlier flowering | Late flowering |
| Flower size: | Medium to large | Medium |
| Flower shape: | Flat | Bit cup shaped |

Plant:
- *Form, growth and habit.*—Mounding plant habit.
- *Plant height.*—16 cm.
- *Plant height (inflorescence included).*—18 cm.
- *Plant diameter (width).*—Approximately 23 cm.

Roots:
- *Number of days to initiate and produce roots.*—15 days at about 22° C.
- *Type.*—Fine, fibrous, free branching.
- *Color.*—RHS N158C.

Foliage:
- *Arrangement.*—Alternate, simple; sometimes opposite, decussate.
- *Immature leaf, color upper surface.*—RHS 137C.
- *Immature leaf, color lower surface.*—RHS 147C.
- *Mature leaf, color upper surface.*—RHS 137B.
- *Mature leaf, color lower surface.*—RHS 147B.
- *Length.*—3.4-4.4 cm.
- *Width.*—2-2.6 cm.
- *Shape.*—Ovate.
- *Base shape.*—Shortly attenuate.
- *Apex shape.*—Acute.
- *Margin.*—Entire.
- *Texture, upper surface.*—Densely covered with short hairs.
- *Lower surface.*—Densely covered with short hairs.
- *Color of veins, upper surface.*—RHS 144A.
- *Color of veins, lower surface.*—RHS 144A.
- *Petiole color.*—RHS 144A.
- *Length.*—0.2 cm.
- *Diameter.*—0.2 cm.
- *Petiole texture.*—Densely covered with short hairs.

Stem:
- *Quantity of main branches per plant.*—4-5.
- *Color of stem.*—RHS 146A.
- *Length of stem.*—14 cm.
- *Diameter.*—0.3 cm.
- *Length of internodes.*—1.4-2.4 cm.
- *Texture.*—Dense, mostly glandular short hairs.
- *Color of pedicel.*—RHS 144A.
- *Length of pedicel.*—2.6 cm.
- *Diameter of pedicel.*—0.3 cm.
- *Texture of pedicel.*—Densely covered with short hairs.

Inflorescence:
- *Type.*—Flowers solitary in upper leaf axis.
- *Floret type.*—Funnel-shaped; 5 lobed petals; fused at base.
- *Blooming habit.*—Medium to late flowering in greenhouse, flowering throughout the summer months.
- *Quantity of inflorescences per plant.*—Approximately 28.
- *Lastingness of individual blooms on the plant.*—About 7 days.
- *Fragrance.*—Rather strong smell.

Bud (just when opening):
- *Color.*—RHS 1A at top, RHS 150A in middle RHS 144A towards base.
- *Length.*—2.4 cm.
- *Width.*—0.5 cm.
- *Shape.*—Oblong.

Immature inflorescence:
- *Flower horizontal diameter.*—5.6 cm.
- *Color petals, upper surface.*—RHS 3B, RHS 4A near throat.
- *Color petals, lower surface.*—RHS 3B.

Mature flower:
- *Flower horizontal diameter.*—6.4 cm.
- *Flower height (vertical).*—3.8 cm.
- *Color upper surface.*—RHS 4B at margin, RHS 4A in middle, RHS 3A near throat.
- *Color lower surface.*—RHS 4B.
- *Conspicuousness of veins.*—Weak.
- *Apex shape.*—Acuminate.
- *Margin.*—Entire.
- *Waviness of margin.*—Medium.
- *Petal lobation.*—Medium.
- *Petal texture, upper surface.*—Smooth.
- *Petal texture, lower surface.*—Smooth, occasionally a short hair.
- *Corolla tube color outside.*—RHS 165D with veins N143C.
- *Corolla tube color inside.*—RHS 164A.
- *Conspicuousness of veins in tube.*—Medium.
- *Corolla tube length.*—2.3 cm.
- *Corolla tube texture, outside.*—Rather dense and short glandular hairs.
- *Corolla tube texture, inside.*—Glabrous.

Calyx:
- *Color of sepal, upper surface.*—RHS 136B.
- *Color of sepal, lower surface.*—RHS 137B.
- *Length.*—1.1 cm.
- *Width.*—0.4 cm.
- *Shape.*—Ensiform.
- *Apex shape.*—Acute.
- *Base.*—Fused.
- *Margins.*—Entire.
- *Texture, upper surface.*—Densely covered with short glandular hairs.
- *Lower surface.*—Densely covered with short glandular hairs.

Reproductive organs:
- *Pistil.*—1.
- *Length.*—2.1 cm.
- *Style color.*—RHS 145C.
- *Style length.*—1.6 cm.
- *Stigma color.*—RHS 149B.
- *Stamens.*—
- *Quantity per flower.*—5.
- *Color of filaments.*—RHS 157C.
- *Length filaments.*—2.1 cm.
- *Anther color.*—RHS 159A.
- *Anther length.*—0.3 cm.
- *Anther shape.*—Elliptical.
- *Color of pollen.*—RHS 158A.
- *Pollen amount.*—Abundant.
- *Fertility/seed set.*—Has not been observed on this hybrid.
- *Disease/pest resistance.*—Has not been observed on this hybrid.

What is claimed is:

1. A new and distinct variety of *Petunia* plant named 'PEHY0092' substantially as illustrated and described herein.

* * * * *